United States Patent [19]

Ishikawa et al.

[11] Patent Number: 5,507,970
[45] Date of Patent: Apr. 16, 1996

[54] DETERGENT COMPOSITION

[75] Inventors: Toshiyuki Ishikawa; Shigeo Nishida; Chisato Ukiya; Hirofumi Kanao, all of Tokyo, Japan

[73] Assignee: Lion Corporation, Tokyo, Japan

[21] Appl. No.: 166,150

[22] Filed: Dec. 14, 1993

Related U.S. Application Data

[63] Continuation of Ser. No. 889,901, May 29, 1992, abandoned.

[51] Int. Cl.$^6$ ............................................. C11D 3/22
[52] U.S. Cl. ............... 252/174.17; 252/173; 252/174.18; 252/DIG. 5; 252/DIG. 13; 252/DIG. 14
[58] Field of Search ................... 252/174.17, 174.18, 252/DIG. 5, DIG. 13

[56] References Cited

U.S. PATENT DOCUMENTS

| | | | |
|---|---|---|---|
| 3,867,301 | 2/1975 | Watanabe et al. | 252/108 |
| 3,872,020 | 3/1975 | Yamagishi et al. | 252/89 |
| 4,187,121 | 2/1980 | Herold et al. | 134/26 |
| 4,395,365 | 7/1983 | Hasegawa et al. | 252/545 |
| 4,800,038 | 1/1989 | Broze et al. | 252/174.17 |
| 4,889,651 | 12/1989 | Broze | 252/95 |
| 5,047,165 | 9/1991 | Lysy et al. | 252/121 |
| 5,047,168 | 9/1991 | Broze et al. | 252/174.17 |
| 5,109,127 | 4/1992 | Sekiguchi et al. | 536/115 |
| 5,190,747 | 3/1993 | Sekiguchi et al. | 424/56 |

FOREIGN PATENT DOCUMENTS

| | | |
|---|---|---|
| 3174497 | 7/1991 | Japan. |
| 3174498 | 7/1991 | Japan. |
| 3185094 | 8/1991 | Japan. |
| 3223398 | 10/1991 | Japan. |
| 4011698 | 1/1992 | Japan. |

OTHER PUBLICATIONS

Derwent abstract of JP 3174497, Jul. 1991.
Derwent abstract of JP 3174498, Jul. 1991.
Derwent abstract of JP 3185094, Aug. 1991.
Derwent abstract of JP 3223398, Oct. 1991.
Derwent abstract of JP 4011698, Jan. 1992.

*Primary Examiner*—Paul Lieberman
*Assistant Examiner*—Ardith Hertzog
*Attorney, Agent, or Firm*—Foley & Lardner

[57] ABSTRACT

A detergent composition comprising:

(i) 0.5 percent to 50 percent by weight, based upon the total weight of the composition, of sugar ester-based surfactants composed of an ester of a fatty acid having 6 to 18 carbon atoms and a monoalkyl ether of monosaccharide having 5 to 6 carbon atoms and (ii) an ester of a fatty acid having 6 to 18 carbon atoms, wherein the weight ratio (ii)/(i) is 0.001 to 0.2, or (i) 0.5 percent to 50 percent by weight, based upon the total weight of the composition, of sugar ester-based surfactants composed of an ester of a fatty acid having 6 to 18 carbon atoms and a monoalkyl ether of monosaccharide having 5 to 6 carbon atoms and (ii) 0.001 to 10 percent by weight, based upon the total weight of the composition, of a monoalkyl ether of monosaccharide or oligosaccharide having 5 to 6 carbon atoms.

1 Claim, No Drawings

DETERGENT COMPOSITION

This application is a continuation of United States application Ser. No. 07/889,901 filed May 29, 1992, now abandoned.

BACKGROUND OF THE INVENTION

1. Field of the Invention

The present invention relates to a detergent composition which is superior in sudsing subsidence and smooths and moisturizes the hand and to a liquid detergent composition superior in low temperature stability.

2. Description of the Related Art

Since kitchen cleaners, household cleaners, shampoos, body shampoos, clothing detergents, and other detergents inevitably contact the skin of the hand etc. during washing, studies have been made in the past to develop detergent composition which are mild to the skin and do not give a greasy feeling.

A sugar ester-based surfactant comprised of an ester of a fatty acid having 6 to 18 carbon atoms and a monoalkyl ether of a monosaccharide having 5 to 6 carbon atoms is known as a surfactant which causes little irritation and is mild to the skin. When such sugar ester-based surfactants are formulated into a detergent, however, there is the problem of a deterioration of the sudsing subsidence, in particular the rinse-off property at low temperatures. Further, detergents having such sugar ester-based surfactants formulated therein have not necessarily been sufficient in terms of the moist feeling given to the skin after use. The moisture of the skin is lost and chaffing due to abrasion and drying is felt. Also, when such sugar ester-based surfactants are formulated into a liquid detergent, the low temperature stability becomes worse. Therefore, when the liquid detergent composition is stored at a low temperature in cold regions etc, the problem of nonhomogenity and turbidity arises.

SUMMARY OF THE INVENTION

Therefore, the object of the present invention is to eliminate the above problems of the prior art and to improve the rinse-off property of a detergent composition in which sugar ester-based surfactants are formulated.

Another object of the present invention is to provide a detergent composition which smooths and moisturizes the hand after washing.

A further object of the present invention is to improve the low temperature stability of a liquid detergent composition in which sugar ester-based surfactants are formulated.

Other objects and advantages of the present invention will be apparent from the following description.

In accordance with the present invention, there is provided a detergent composition comprising (i) 0.5 percent to 50 percent by weight, based upon the total weight of the composition, of sugar ester-based surfactants composed of an ester of a fatty acid having 6 to 18 carbon atoms and a monoalkyl ether of a monosaccharide having 5 to 6 carbon atoms and (ii) an ester of a fatty acid having 6 to 18 carbon atoms, the weight ratio (ii)/(i) being 0.001 to 0.2.

In accordance with the present invention, there is also provided a detergent composition comprising:

(i) 0.5 percent to 50 percent by weight, based upon total weight of the composition, of sugar ester-based surfactants composed of an ester of a fatty acid having 6 to 18 carbon atoms and a monoalkyl ether of a monosaccharide having 5 to 6 carbon atoms and (ii) 0.001 to 10 percent by weight, based upon the total weight of the composition, of a monoalkyl ether of a monosaccharide or oligosaccharide having 5 to 6 carbon atoms.

DESCRIPTION OF THE PREFERRED EMBODIMENTS

The sugar ester-based surfactants of the component (i) in the first and second aspects of the present invention are surfactants which cause little irritation and are mild to the skin, which are obtained from a fatty acid having 6 to 18 carbon atoms (or a fatty acid derivative such as an ester of the fatty acid) and a monoalkyl ether of a monopentose or monohexose.

Here, the fatty acid may be saturated or unsaturated or straight chain or branched. Specific examples of such a fatty acid are caproic acid, caprylic acid, capric acid, lauric acid, myristic acid, palmitic acid, stearic acid, caproleic acid, lauroleic acid, myristoleic acid, palmitoleic acid, oleic acid, and methylundecanoic acid.

Further, examples of fatty acid derivatives are the fatty acid ester of the above fatty acids and lower alcohol such as, for example, the methyl ester, ethyl ester, propyl ester, etc. of the above-mentioned fatty acids.

Examples of monoalkyl ethers of monopentose are xylose, arabinose, ribose, xylulose, lyxose, and other methyl, ethyl, and other monoalkyl ether compounds of a monopentose. Examples of the alkyl ether of a monohexose are methyl, ethyl, and other monoalkyl ether compounds of glucose, mannose, galactose, fructose, and other monohexoses.

The sugar ester-based surfactants of the present invention are preferably a monoester/diester type mixture including a monoester type and diester type where a fatty acid residue having 6 to 18 carbon atoms is ester-bonded to a hydroxy group of an alkyl ether compound of a monosaccharide, wherein the polyesters of triesters or higher esters are desirably not more than 1 percent by weight.

The sugar ester-based surfactants of the component (i) are included in the detergent composition of the present invention in an amount of 0.5 to 50 percent by weight, preferably 1 to 25 percent by weight. When the amount contained is too small, the cleaning effect and the effect of improvement of the greasy feeling are not sufficiently obtained. On the other hand, even if the amount contained is made large, no improvement is seen in the cleaning performance and the stability of the system is also degraded.

In the first aspect of the present invention, it is necessary to formulate an ester of a fatty acid having 6 to 18 carbon atoms and sugar of component (ii) in a ratio of weight (ii)/(i) with respect to the sugar ester-based surfactants of the component (i) of 0.001 to 0.2, preferably 0.01 to 0.15. By formulating the sugar ester of the component (i) in an amount of at least 0.001 in terms of the weight ratio, the rinse-off property at low temperature is improved. On the other hand, when the weight of the sugar ester exceeds 0.2 in weight ratio, the cleaning performance decreases remarkably and so this is not preferable.

The sugar ester of the component (ii) can be obtained from a fatty acid and sugar. Here, the fatty acid, as in the case of the fatty acid used in the sugar ester-based surfactants of component (i), may be saturated or unsaturated and may be straight chain or branched.

Examples of the sugar xylose, arabinose, ribulose, ribose, glucose, mannose, galactose, fructose, and other monosaccharides, maltose, lactose, sucrose, and other bisaccharides, raffinose, stachyose, and other oligosaccharides of $(C_6H_{10}O_5)n$ (where n=3 to 6).

The sugar ester of the component (ii) is not limited as to the number of ester bonds so long as it is a sugar ester, but a mono- to tri-ester is preferable, more preferably a monoester.

Examples of the monosaccharide or oligosaccharide or monosaccharide of an alkyl ether of the same of the component (ii) in the second aspect of the present invention are xylose, arabinose, ribulose, xylulose, lyxose, and other monopentoses, glucose, mannose, galactose, fructose, and other monohexoses, etc.

Further, as the oligosaccharide, use may be made of an oligosaccharide comprised of two to six monosaccharide units having 5 to 6 carbon atoms bonded together, preferably an oligosaccharide with two to four monosaccharide units bonded together. As specific examples of these oligosaccharides, mention may be made, for example, of sucrose, altose, lactose, trehalose, cellobiose, isomaltose, gentiobiose, gentianose, raffinose, stachyose, maltotriose, maltotetraose, maltopentose, etc.

Further, examples of the alkyl ethers of the same are mono-, di-, and tri-alkyl ethers, etc., preferably monoalkyl ethers. Specific examples of such alkyl ethers are methyl xylose, ethyl arabinose, and other monopentose monoalkyl compounds (monoalkyl ethers), methyl glucose, ethyl glucose, ethyl lactose, methyl trehalose, and other oligosaccharide alkyl ethers.

The monosaccharide or the oligosaccharide and alkyl ether of the same of the component (ii) of the second aspect of the present invention is formulated into the detergent composition in an amount of 0.001 to 10 percent by weight, preferably 0.1 to 8 percent by weight. When the component (ii) is added in an amount of over 0.001 percent by weight, the skin of the hand is made to feel smooth and moist after washing. On the other hand, when the component (ii) is formulated in an amount of more than 10 percent by weight, the stability of the detergent composition with respect to contamination by microorganisms is deteriorated.

The liquid detergent composition according to the present invention contains the following components (a) and (b) in a ratio of weight of (a)/(b) of 1/9 or more:

(a) Sugar ester-based surfactants comprised of an ester of a fatty acid having 6 to 8 carbon atoms and a monosaccharide having 5 to 6 carbon atoms or a monoalkyl ether of the same, (b) Sugar ester-based surfactants comprised of an ester of a fatty acid having 10 to 12 carbon atoms and a monosaccharide having 5 to 6 carbon atoms or a monoalkyl ether of the same.

The sugar ester-based surfactants of the components (a) and (b) are surfactants which cause little irritation and are mild to the skin. When, however, only the sugar ester-based surfactants of the component (b), where the fatty acid residues have a chain of 10 to 12 carbon atoms in length, are formulated to form a liquid detergent composition, the long term storage stability at low temperature is poor. Contrarily, the low temperature stability can be improved by using mixed in a ratio of weight of (a)/(b) of 1/9 or more, preferably (a)/(b) of 2/8 to 6/4, the sugar ester-based surfactants of the component (a), where the fatty acid residues have 6 to 8 carbon atoms. Further, when the sugar ester-based surfactants of the component (b) are not used, but only the component (a) is formulated into the liquid detergent composition, the cleaning performance deteriorates slightly.

The sugar ester-based surfactants of the component (a) and the component (b) are both formulated into the liquid detergent composition of the present invention preferably in an amount of 1 to 30 percent by weight, more preferably 5 to 25 percent by weight. When the amount of intermixture is too small, the cleaning effect and the effect of improvement of the greasy feeling cannot be sufficiently obtained. On the other hand, even if the amount of mixture is made larger, no improvement in the cleaning performance is seen and the stability of the system deteriorates.

The sugar ester-based surfactants of the component (a) and the component (b) are obtained from a fatty acid of a predetermined number of carbon atoms or a fatty acid derivative such as an ester of the fatty acid and a monopentose, monohexose, or monoalkyl ether of the same.

Here, the fatty acid may be saturated or unsaturated or straight chain or branched. Specific examples of the fatty acid of the component (a) are caproic acid, caprylic acid, etc. Further, specific Examples of the fatty acid in the component (b) are capric acid, lauric acid, methyl undecanic acid, caproleic acid, lauroleic acid, myristoleic acid, palmitoleic acid, etc.

Further, the fatty acid derivatives usable in the present invention include fatty acid esters of the above-mentioned fatty acids and lower alcohols, for example, methyl esters, ethyl esters, propyl esters, etc. of the above-mentioned fatty acids.

Examples of the monopentose usable in the present invention are xylose, arabinose, ribulose, xylulose, lyxose, and other monopentoses and also methyl xylose, ethyl arabinose, and other monoalkyl compounds (monoalkyl ethers). Examples of the monohexose are glucose, mannose, galactose, fructose, and other monohexoses and also methyl glucose, ethyl glucose, and other monoalkyl compounds (monoalkyl ethers).

The sugar ester-based surfactants of the components (a) and (b) of the present invention preferably have as their main components monoesters comprised of fatty acid residues ester-bonded to a hydroxy group of a monosaccharide, more preferably one where the polyesters of the triester or higher esters are in an amount of not more than 1 percent by weight.

It is possible to suitably add in the liquid detergent composition of the present invention various components depending upon a desired application, for example, anionic surfactants, nonionic surfactants, cationic surfactants, bipolar surfactants, and other surfactants or other additives.

Examples of the anionic surfactants are as follows;

1) Alkyl sulfuric acid salts of 10 to 18 carbon atoms

2) Alkane sulfonic acid salts of 10 to 18 carbon atoms

3) Olefin sulfonic acid salts of 10 to 18 carbon atoms

4) Alkyl benzene sulfonic acid salts of 10 to 18 carbon atoms in the alkyl group 5) Polyoxyethylene alkyl (or alkenyl) ether sulfuric acid salts (average number of added moles of the ethylene oxide of 2 to 7) of 10 to 18 carbon atoms in the alkyl group or alkenyl group 6) Sulfonic acid salts of lower alkyl esters of fatty acids (number of carbon atoms of fatty acid of 10 to 20, number of carbon atoms of alkyl group of 1 to 3)

Examples of such salts are alkaline metal salts, alkaline earth metal salts, ammonium salts, alkanol amine salts, etc.

In addition, it is possible to add polyoxyethylene alkyl ethers, polyoxyethylene•polyoxypropylene alkyl ethers, alkyl amine oxides, alkanol amines, fatty acid alkanol amides, lower alcohols, polyhydric alcohols, lower aryl sulfonic acid salts, and other hydrotropic agents; zeolite and other inorganic builders, ethylenediamine 4-acetic acid salt, diethylene triamine 5-acetic acid salt, and other metal ion sequestering agents; carbonic acid salts, silicic acid salts, and other alkali builders; benzoic acid and other antibacterial agents, protease, lipases, cellulase, amylase, and other enzymes; colorants, fragrances, and the like.

The detergent composition of the present invention can be used as a detergent for various applications, but it is particularly suited to applications where the detergent composition comes into contact with the hand, skin, scalp, etc. and for washing hard surfaces such as of dishes, tile, and glass. For example, it is suitably used for shampoos, body shampoos, kitchen cleaners, bathtub cleaners, toilet cleaners, and other household cleaners, clothing detergents, etc.

According to the first aspect of the present invention, when use is made of a sugar ester-based surfactant comprised of an ester of a fatty acid and a monoalkyl ether of a monosaccharide, it is possible to improve the rinse-off property of the detergent composition including the sugar ester-based surfactants by making joint use of a sugar ester. The result is superior in terms of the product quality.

According to the second aspect of the present invention, by making joint use of (a) a sugar ester-based surfactant comprised of an ester of a fatty acid and a monoalkyl ether of a monosaccharide and (b) a saccharide or its monoalkyl ether, it is possible to retain the moisture of the skin and give a moist feeling to the hand and to prevent chaffing due to abrasion and drying.

According to the liquid detergent composition of the present invention, by mixing (a) sugar ester-based surfactants comprised of fatty acid residues of 6 to 8 carbon atoms ester-bonded and (b) sugar ester-based surfactants comprised of fatty acid residues of 10 to 12 carbon atoms ester-bonded within a predetermined range of amounts, it is possible to improve the low temperature stability of the liquid detergent composition including the sugar ester-based surfactant. Therefore, even in cold regions, it is possible to stably store the liquid detergent composition and there is no turbidity etc., so this is superior in terms of the product quality.

EXAMPLES

The present invention will now be further illustrated by, but is by no means limited to, the following examples;

EXAMPLE 1

The detergents of the compositions shown in Table 1 to Table 3 were prepared and evaluated as to their sudsing subsidence. The results are shown in Table 1 to Table 3. Note that the indication of "$C_{10}$ methyl glucose ester" etc. in the sugar ester-based surfactants in the Tables means "an ester of a fatty acid having 10 carbon atoms and methyl glucose" etc. In the same way, the indication of "$C_8$ glucose monoester" etc. in the sugar esters means a "monoester of a fatty acid having 8 carbon atoms and glucose".

Further, the other symbols or descriptions in the tables are as follows:

$C_{11}$ to $C_{13}$ AS-Na: Sodium alkyl sulfate having 11 to 13 carbon atoms $C_{12}$ to $C_{14}$ AES-Na (p=3): sodium polyoxyethylene (average number of added moles of 3) alkyl (12 to 14 carbon atoms) ether sulfate $C_{10}$ to $C_{18}$ AOS-Na: Sodium α-olefin sulfonate having 10 to 18 carbon atoms $C_{12}$ to $C_{14}$ LAS-Na: Sodium straight chain alkyl (12 to 14 carbon atoms) benzene sulfonate POE (p=12) $C_{12}$ alkyl ether: Polyoxyethylene (average number of added moles of 12) alkyl (12 carbon atoms) ether POE (p=12)•POP (p=5) $C_{12}$ alkyl ether: Polyoxyethylene (average number of added moles of 12)•polyoxypropylene (average number of added moles of 5) alkyl (12 carbon atoms) ether Common components

| | |
|---|---|
| Lauryl dimethyl amine oxide | 2.5 wt % |
| Coconut fatty acid diethanol amide | 0.2 wt % |
| Ethanol | 2.5 wt % |
| Sodium benzoate | 1.0 wt % |
| Sodium toluene sulfonate | 5.0 wt % |
| Total | 11.2 wt % |

Method of Evaluation of Sudsing Subsidence

A 10 percent by weight benzene solution of organic dirt containing the following dirt components was uniformly spread on a cotton T-shirt in an amount with respect to the fibers of 0.1 percent by weight. This was air dried, and the following evaluation was performed.

A 0.14 percent tap water solution of the detergent composition was prepared in a washing machine (whirlpool and reversing type). The above dirtied cotton T-shirt was used as the fabric to be washed. It was washed by the usual operation in a bath ratio of 1:30 at 15° C., then the washed fabric was spin dried for one minute, then rinsed by running water (15 liters/min) not containing the detergent composition. The time required until the suds disappeared was measured.

| Dirt component | Dirt composition (wt %) |
|---|---|
| Cholesterol oleate | 17.3 |
| Liquid paraffin | 3.6 |
| Squalene | 3.6 |
| Cholesterol | 2.3 |
| Gelatin | 10.0 |

TABLE 1

| Composition | Sample no. (wt % below) | | | | | | | |
|---|---|---|---|---|---|---|---|---|
| | 1 | 2 | 3 | 4 | 5 | 6 | 7 | 8 |
| $C_{10}$ methyl glucose ester | 10 | — | — | — | — | — | — | — |
| $C_{10}$ methyl fructose ester | — | 10 | — | — | — | — | — | — |
| $C_{10}$ methyl xylose ester | — | — | 10 | — | — | — | — | — |
| $C_{10}$ methyl mannose ester | — | — | — | 10 | — | — | — | — |

TABLE 1-continued

| Composition | Sample no. (wt % below) | | | | | | | |
| --- | --- | --- | --- | --- | --- | --- | --- | --- |
| | 1 | 2 | 3 | 4 | 5 | 6 | 7 | 8 |
| $C_{10}$ ethyl glucose ester | — | — | — | — | 10 | — | — | — |
| $C_{10}$ ethyl fructose ester | — | — | — | — | — | 10 | — | — |
| $C_{10}$ ethyl xylose ester | — | — | — | — | — | — | 10 | — |
| $C_{10}$ ethyl mannose ester | — | — | — | — | — | — | — | 10 |
| $C_8$ glucose monoester | 0.5 | — | — | — | — | — | — | 0.5 |
| $C_8$ glucose diester | — | 0.5 | — | — | — | — | — | — |
| $C_8$ glucose triester | — | — | 0.5 | — | — | — | — | — |
| $C_8,C_{10}$ glucose diester | — | — | — | 0.5 | — | — | — | — |
| $C_{10}$ maltose monoester | — | — | — | — | 0.5 | — | — | — |
| $C_8$ stachyose monoester | — | — | — | — | — | 0.5 | — | — |
| $C_8$ malto-hexaose monoester | — | — | — | — | — | — | 0.5 | — |
| $C_{11}$ to $C_{13}$ AS—Na | 5 | 5 | 5 | 5 | 5 | — | — | — |
| $C_{12}$ to $C_{14}$ AES—Na (p = 3) | — | — | — | — | — | 5 | 5 | 5 |
| POE(p = 12) · POP(p = 5) $C_{12}$ alkyl ether | 2 | 2 | 2 | 2 | 2 | 2 | 2 | 2 |
| Common component | 11.2 | 11.2 | 11.2 | 11.2 | 11.2 | 11.2 | 11.2 | 11.2 |
| Water | Bal. | Bal. | Bal. | Bal. | Bal. | Bal. | Bal. | Bal. |
| Sudsing subsidence (required time in minutes) | 15 | 15 | 15 | 15 | 15 | 15 | 15 | 15 |

TABLE 2

| Composition | No. of sample (wt % below) | | | | | | | |
| --- | --- | --- | --- | --- | --- | --- | --- | --- |
| | 9 | 10 | 11 | 12 | 13 | 14 | 15 | 16 |
| $C_{10}$ methyl glucose ester | — | — | — | — | — | — | — | 5 |
| $C_{10}$ ethyl mannose ester | 10 | — | — | — | — | — | — | — |
| $C_8$ ethyl glucose ester | — | 10 | — | — | — | — | — | 5 |
| $C_8$ methyl glucose ester | — | — | 10 | — | — | — | — | — |
| $C_{14}$ ethyl glucose ester | — | — | — | 10 | — | — | — | — |
| $C_{14}$ methyl glucose ester | — | — | — | — | 10 | — | — | — |
| $C_{18}$ ethyl glucose ester | — | — | — | — | — | 10 | — | — |
| $C_{18}$ methyl glucose ester | — | — | — | — | — | — | 10 | — |
| $C_8$ glucose monoester | 0.5 | — | — | — | — | — | — | 0.5 |
| $C_8$ glucose diester | — | 0.5 | — | — | — | — | — | — |
| $C_8$ glucose triester | — | — | 0.5 | — | — | — | — | — |
| $C_8,C_{10}$ glucose diester | — | — | — | 0.5 | — | — | — | — |
| $C_{10}$ maltose monoester | — | — | — | — | 0.5 | — | — | — |
| $C_8$ stachyose monoester | — | — | — | — | — | 0.5 | — | — |
| $C_8$ malto-hexaose monoester | — | — | — | — | — | — | 0.5 | — |
| $C_{10}$ to $C_{18}$ AOS—Na | 3 | 3 | 3 | — | — | — | — | — |
| $C_{12}$ to $C_{14}$ LAS—Na | — | — | — | 3 | 3 | 3 | — | — |
| POE (p = 12) · $C_{12}$ alkyl ester | — | — | — | — | — | — | 5 | 5 |
| POE(p = 12) · POP p = 5) $C_{12}$ alkyl ester | 2 | 2 | 2 | 2 | 2 | 2 | 2 | 2 |
| Common component | 11.2 | 11.2 | 11.2 | 11.2 | 11.2 | 11.2 | 11.2 | 11.2 |
| Water | Bal. | Bal. | Bal. | Bal. | Bal. | Bal. | Bal. | Bal. |
| Sudsing subsidence (required time in minutes) | 12 | 12 | 12 | 17 | 17 | 17 | 10 | 10 |

TABLE 3

| Composition | No. of sample (wt % below) | | | | | |
| --- | --- | --- | --- | --- | --- | --- |
| | 17 | 18 | 19 | 20 | 21 | 22 |
| $C_{10}$ methyl glucose ester | 2 | 20 | 40 | 10 | 10 | 10 |
| $C_{10}$ glucose monoester | — | — | 4 | 0.1 | 1 | 1.5 |
| $C_8$ glucose diester | 0.2 | — | — | — | — | — |
| $C_{10}$ maltose monoester | — | 2 | — | — | — | — |
| $C_{11}$ to $C_{13}$ AS—Na | — | — | — | 5 | — | — |
| $C_{12}$ to $C_{14}$ AES—Na (p = 3) | 5 | — | — | — | — | — |
| $C_{10}$ to $C_{18}$ AOS—Na | — | 2 | — | — | 5 | — |
| $C_{12}$ to $C_{14}$ LAS—Na | — | — | 2 | — | — | 5 |
| POE (p = 12) · $C_{12}$ alkyl ester | 5 | — | — | 5 | — | — |
| POE (p = 12) · POP (p = 5) $C_{12}$ alkyl ester | — | 5 | 5 | — | 5 | 5 |
| Common component | 11.2 | 11.2 | 11.2 | 11.2 | 11.2 | 11.2 |
| Water | Bal. | Bal. | Bal. | Bal. | Bal. | Bal. |
| Sudsing subsidence (required time in minutes) | 10 | 12 | 15 | 10 | 10 | 12 |

| (1) Shampoo composition | |
|---|---|
| $C_8/C_{10}$ = 1:1 methyl glucose ester | 15.0 wt % |
| $C_8$ glucose monoester | 1.0 wt % |
| Amine oxide | 3.0 wt % |
| Polymer JR-400 (made by Union Carbide) | 0.2 wt % |
| Behenyl trimethyl ammonium chloride (average molecular weight 404) | 2.42 wt % |
| Propylene glycol | 5.0 wt % |
| Polyoxyethylene (average 40 moles) hardened castor oil derivative | 2.0 wt % |
| N-lauryl dimethyl amino acetic acid betaine | 5.0 wt % |
| Colorants and fragrances | q.s. |
| Ion exchange water | Balance |

| (2) Shampoo composition | |
|---|---|
| $C_8$ ethyl glucose ester | 7.0 wt % |
| $C_{10}$ glucose diester | 0.1 wt % |
| Sodium polyoxyethyelene lauryl ether sulfate (p = 3, alkyl group $C_{12}/C_{13}$ = 1/1) | 5.0 wt % |
| Dimethyl polysiloxane (100,000 cs) | 2.0 wt % |
| Yukaformer AM75201 | 2.0 wt % |
| Imidazolinium betaine (alkyl group: coconut) | 5.0 wt % |
| Stearyl trimethyl ammonium chloride | 1.0 wt % |
| Quaternary nitrogen-containing cellulose ether (nitrogen content 2.0 percent, molecular weight 100,000) | 0.5 wt % |
| Coconut oil fatty acid diethanol amide | 2.0 wt % |
| Fragrance | 0.4 wt % |
| Colorant (Yellow #203) | Trace |
| Citric acid | pH 5.8 adjust. |
| Purified water | Balance |

| (3) Shampoo composition | |
|---|---|
| $C_8$ methyl glucose ester | 10.0 wt % |
| $C_{10}$ maltose monoester | 1.5 wt % |
| Sodium $C_{12}$, $C_{13}$ alkyl sulfate | 5.0 wt % |
| Sodium $C_{10}$ to $C_{18}$ α-olefin sulfonate | 5.0 wt % |
| Polyoxyethyelene lauryl ether (p = 7) | 2.0 wt % |
| Paraffin sulfonate | 4.0 wt % |
| Dimethyl polysiloxane (10,000 cs) | 2.0 wt % |
| Dimethyl polysiloxane (100,000 cs) | 1.0 wt % |
| Yukaformer AM75201 | 2.0 wt % |
| Yukaformer AMW | 0.5 wt % |
| Imidazolinium betaine (alkyl group: coconut) | 1.0 wt % |
| Stearyl trimethyl ammonium chloride | 0.5 wt % |
| Quaternary nitrogen-containing cellulose ether (nitrogen content 2.0 percent, molecular weight 100,000) | 0.3 wt % |
| Coconut oil fatty acid diethanol amide | 2.0 wt % |
| Fragrance | 0.4 wt % |
| Colorant (Yellow #203) | Trace |
| Citric acid | pH 5.8 adjust. |
| Purified water | Balance |

| (4) Body shampoo composition | |
|---|---|
| $C_{10}$ methyl glucose ester | 30.0 wt % |
| $C_8$ stachyose ester | 0.5 wt % |
| Sodium $C_{12}$, $C_{13}$ alkyl sulfate | 1.0 wt % |
| Sodium $C_{10}$ to $C_{18}$ α-olefin sulfonate | 1.0 wt % |
| Sodium $C_{12}$ alanynate | 0.5 wt % |
| $C_{15}$ alkyl succinic acid sodium | 1.0 wt % |
| Polyoxyethyelene lauryl ether (p = 12) | 1.0 wt % |
| Soap | 0.5 wt % |
| Lauroyl salcosin sodium (average molecular weight of 310) | 0.93 wt % |
| Lauryl imidazolinium betaine | 10.0 wt % |
| Dipropylene glycol | 8.0 wt % |
| Aloe extract | 0.5 wt % |
| Colorants and fragrances | q.s. |
| Preservative and chelating agent | q.s. |
| Ion exchange water | Balance |

| (5) Body shampoo composition | |
|---|---|
| $C_{10}$ methyl glucose ester | 30.0 wt % |
| $C_8$ xylose diester | 1.0 wt % |
| $C_{14}$ monoalkyl dimethyl amine dioxide | 2.5 wt % |
| Sodium coconut oil fatty acid methyl- β-alanine | 3.0 wt % |
| Lauryl imidazolinium betaine | 10.0 wt % |
| Dipropylene glycol | 8.0 wt % |
| Aloe extract | 0.5 wt % |
| Colorants and fragrances | q.s. |
| Preservative and chelating agent | q.s. |
| Ion exchange water | Balance |

| (6) Clothing use liquid detergent composition | |
|---|---|
| $C_{10}$ methyl glucose ester | 20.0 wt % |
| $C_8$, $C_{10}$ glucose ester | 4.0 wt % |
| Sodium $C_{12}$, $C_{13}$ alkyl sulfate | 5.0 wt % |
| Sodium $C_{10}$ to $C_{18}$ α-olefin sulfonate | 5.0 wt % |
| Sodium $C_{12}$ alanynate | 3.0 wt % |
| Sodium $C_{15}$ alkyl succinate | 3.0 wt % |
| Polyoxyethylene lauryl ether (p = 12) | 1.0 wt % |
| Soap | 2.0 wt % |
| Sodium xylene sulfonate | 5.0 wt % |
| Lauryol alanine sodium (average molecular weight 307) | 3.05 wt % |
| Lauryl dimethyl amino acetic acid betaine | 5.0 wt % |
| Fluorescent dye | 0.2 wt % |
| Ethanol | 8.0 wt % |
| Colorants and fragrances | q.s. |
| Sodium hydroxide | q.s. |
| Ion exchange water | Balance |

(7) Clothing use granular detergent composition

| Composition | Sample (wt % below) | | | |
|---|---|---|---|---|
| | A | B | C | D |
| $C_{10}$ methyl glucose ester | 5 | 10 | 5 | 5 |
| $C_8$ glucose monoester | 0.5 | 1 | 0.5 | 0.5 |
| α-sulfo palm fatty acid methyl ester sodium salt | 5 | — | 15 | — |
| Sodium straight chain alkyl ($C_{12}$ to $C_{13}$) benzene sulfonate | 17 | 12 | 4 | 20 |
| Sodium $C_{14}$ to $C_{18}$ α-olefin sulfonate | — | — | 3 | 12 |
| Soap | 1 | 1 | 1 | 1 |
| Sodium carbonate | 10 | 10 | 10 | 10 |
| Sodium silicate | 3 | 3 | 3 | 6 |
| 4A type zeolite (average particle size 3.5μ) | 15 | 15 | 15 | 15 |
| POE (p = 12) · POP (p = 5) $C_{12}$ alkyl ether | — | — | — | 2 |
| Polyethylene glycol (average molecular weight 13,000) | 2 | 2 | 2 | — |
| Fragrance | 0.005 | 0.02 | 0.01 | 0.02 |
| Enzyme*[1] | 0.4 | 0.4 | 0.3 | 0.4 |
| Sodium sulfate | Bal. | Bal. | Bal. | Bal. |

*[1]Alkali protease:Lipase = 1:1 mixture

EXAMPLE 3

The liquid detergents of the compositions shown in Table 4 and Table 5 were prepared and the moist feeling of the hand was evaluated. The results are shown in Table 4 and Table 5. Note that the indication of "$C_8$ methyl glucose ester" etc. in the sugar ester-based surfactants of the tables means "ester of fatty acid having 8 carbon atoms and methyl glucose" etc.

Method of evaluation of Moistness of hand

The hand was immersed for 5 minutes in a 10 percent by weight aqueous solution of the composition, then was rinsed with running water and dried with a towel. The moist feeling at that time was evaluated by the senses based on the following standards. The scores used were the average values of a 5 member panel. Here, a moist feeling means the retention of moisture of the skin and no feeling of chaffing due to abrasion or drying.

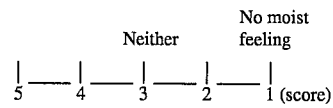

TABLE 4

| Composition | No. of sample (wt % below) | | | | |
|---|---|---|---|---|---|
| | 1 | 2 | 3 | 4 | 5 |
| Component (a) | | | | | |
| $C_8$ methyl glucose ester | 10 | 10 | — | — | 10 |
| $C_{10}$ ethyl xylose ester | — | — | 10 | — | — |
| $C_{12}$ methyl mannose ester | — | — | — | 10 | — |
| Component (b) | | | | | |
| Glucose | 0.1 | — | — | — | — |
| Xylose | — | — | 2 | — | — |
| Mannose | — | — | — | 5 | — |
| Methyl glucose | — | 1 | — | — | — |
| Maltotriose | — | — | — | — | 5 |
| Optional components | | | | | |
| Sodium $C_{11}$, $C_{13}$ alkyl sulfate | 5 | 5 | — | — | 5 |
| Sodium $C_{12}$, $C_{13}$ alkyl ether sulfate | — | — | 5 | — | — |
| Sodium $C_{10}$ to $C_{18}$ α-olefin sulfonate | — | — | — | 0.5 | — |
| Higher alcohol polyoxyethylene ether (p = 12)*1 | — | — | — | 5 | — |
| Lauryl dimethyl amine oxide | 2 | 2 | 2 | 2 | 2 |
| Coconut fatty acid diethanol amide | 5 | 5 | 5 | 5 | 5 |
| Ethanol | 5 | 5 | 5 | 5 | 5 |
| Sodium benzoate | 2 | 2 | 2 | 2 | 2 |
| Sodium toluene sulfonate | 2 | 2 | 2 | 2 | 2 |
| Water | Bal | Bal | Bal | Bal | Bal |
| Moist feeling of hand (average score) | 4.4 | 4.6 | 4.6 | 4.8 | 4.8* |

¹p indicates the average added moles of ethylene oxide.

TABLE 5

| Composition | No. of sample of Ex. 3 (wt % below) | | | | |
|---|---|---|---|---|---|
| | 6 | 7 | 8 | 9 | 10 |
| Component (a) | | | | | |
| $C_8$ methyl glucose ester | 15 | 15 | — | 10 | 10 |
| $C_{10}$ ethyl xylose ester | — | — | 15 | — | — |
| $C_{12}$ methyl mannose ester | — | — | — | — | — |
| Component (b) | | | | | |
| Glucose | 3 | — | — | — | — |
| Xylose | — | — | 7 | — | — |
| Mannose | — | — | — | — | — |
| Lactose | — | — | — | — | 2 |
| Methyl glucose | — | 7 | — | — | — |
| Ethyl maltose | — | — | — | 2 | — |
| Optional components | | | | | |
| Sodium $C_{11}$, $C_{13}$ alkyl sulfate | — | — | — | 5 | — |
| Sodium $C_{12}$, $C_{13}$ alkyl ether sulfate | — | — | — | — | — |
| Sodium $C_{10}$ to $C_{18}$ α-olefin sulfonate | — | — | — | — | — |
| Higher alcohol polyoxyethylene ether (p = 12) | — | — | — | — | 5 |
| Lauryl dimethyl amine oxide | 2 | 2 | 2 | 2 | 2 |
| Coconut fatty acid diethanol amide | 5 | 5 | 5 | 5 | 5 |
| Ethanol | 5 | 5 | 5 | 5 | 5 |
| Sodium benzoate | 2 | 2 | 2 | 2 | 2 |
| Sodium toluene sulfonate | 2 | 2 | 2 | 2 | 2 |
| Water | Bal | Bal | Bal | Bal | Bal |
| Moist feeling of hand (average score) | 4.8 | 4.8 | 4.8 | 4.5 | 4.6 |

EXAMPLE 4

The liquid detergents of the compositions shown in Table 6 and Table 7 were prepared and the low temperature stabilities were evaluated. The results are shown in Table 6 and Table 7. Note that the indication of "$C_8$ glucose ester" etc. in the sugar ester-based surfactants the tables means "an ester of a fatty acid with 6 carbon atoms and glucose".

Method of evaluation of low temperature stability

The liquid detergent composition was filled in a 100 ml glass bottle and allowed to stand at −5° C. for one month, then the outside appearance was evaluated.

TABLE 6

| Composition | No. of sample of Ex. 4 (wt % below) | | | | |
|---|---|---|---|---|---|
| | 1 | 2 | 3 | 4 | 5 |
| Component (a) | | | | | |
| $C_8$ glucose ester | 2 | — | — | — | — |
| $C_8$ methyl glucose ester | — | 5 | 5 | 10 | — |
| $C_8$ xylose ester | — | — | — | — | 10 |
| Component (b) | | | | | |
| $C_{10}$ glucose ester | 8 | 10 | — | — | — |
| $C_{10}$ methyl glucose ester | — | — | 10 | 10 | — |
| $C_{12}$ xylose ester | — | — | — | — | 10 |
| Optional components | | | | | |
| Sodium $C_{11}$, $C_{13}$ alkyl ether sulfate (p = 3) | 5 | 5 | — | — | — |
| Sodium $C_{12}$, $C_{13}$ alkyl sulfate | — | — | 5 | 5 | — |
| Sodium $C_{10}$ to $C_{18}$ α-olefin sulfonate | — | — | — | — | 0.5 |
| Higher alcohol polyoxyethylene ether (p = 12)*1 | — | — | — | — | 5 |
| Lauryl dimethyl amine oxide | 2 | 2 | 2 | 2 | 2 |
| Coconut fatty acid diethanol amide | 5 | 5 | 5 | 5 | 5 |
| Ethanol | 5 | 5 | 5 | 5 | 5 |
| Sodium benzoate | 2 | 2 | 2 | 2 | 2 |
| Sodium toluene sulfonate | 1.5 | 1.5 | 1.5 | 1.5 | 1.5 |
| Water | Bal | Bal | Bal | Bal | Bal |
| (a)/(b) ratio (wt ratio) | 1/4 | 1/2 | 1/2 | 1/1 | 1/1 |
| Low temperature stability | Even | Even | Even | Even | Even |

TABLE 6-continued

| | No. of sample of Ex. 4 (wt % below) | | | | |
|---|---|---|---|---|---|
| Composition | 1 | 2 | 3 | 4 | 5 |
| (−5° C. × 1 month) | | | | | |

*[1] p indicates average number of added moles of ethylene oxide.

TABLE 7

| | No. of sample of comparative example | |
|---|---|---|
| Composition | 6 | 7 |
| Component (a) | | |
| $C_8$ glucose ester | — | — |
| $C_8$ methyl glucose ester | — | — |
| $C_8$ xylose ester | — | — |
| Component (b) | | |
| $C_{10}$ glucose ester | — | — |
| $C_{10}$ methyl glucose ester | 10 | — |
| $C_{12}$ xylose ester | — | 10 |
| Optional components | | |
| Sodium $C_{11}$, $C_{13}$ alkyl ether sulfate (p = 3) | — | — |
| Sodium $C_{12}$, $C_{13}$ alkyl sulfate | 5 | — |
| Sodium $C_{10}$ to $C_{18}$ α-olefin sulfonate | — | 1 |
| Higher alcohol polyoxyethylene ether (p = 12)*[1] | — | 5 |
| Lauryl dimethyl amine oxide | 2 | 2 |
| Coconut fatty acid diethanol amide | 5 | 10 |
| Ethanol | 5 | 5 |
| Sodium benzoate | 2 | 2 |
| Sodium toluene sulfonate | 1.5 | 2 |
| Water | Bal. | Bal. |
| (a)/(b) ratio (wt ratio) | 0 | 0 |
| Low temperature stability (−5° C. × 1 month) | White turbid | White turbid |

*[1] p indicates average number of added moles of ethylene oxide.

We claim:

1. A detergent composition comprising:

(a) 0.5% to 50% by weight, based upon total weight of the composition, of at least one compound selected from the group consisting of $C_8$ methyl glucose ester, $C_{10}$ ethyl xylose ester and $C_{12}$ methyl mannose ester, and (b) 0.001% to 10% by weight, based upon the total weight of the composition, of at least one compound selected from the group consisting of glucose, xylose, mannose, methyl glucose, ethyl maltose, and maltotriose.

* * * * *